US00PP12203P2

(12) United States Plant Patent
Sato

(10) Patent No.: US PP12,203 P2
(45) Date of Patent: Nov. 13, 2001

(54) LOROPETALUM PLANT NAMED 'HINDWARF'

(75) Inventor: Noboru Sato, Saitama (JP)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 09/300,579

(22) Filed: Apr. 27, 1999

(51) Int. Cl.[7] ..... A01H 5/00
(52) U.S. Cl. ..... Plt./226
(58) Field of Search ..... Plt./226

(56) References Cited

U.S. PATENT DOCUMENTS

P.P. 11,766 * 2/2001 Head ..... Plt./226

* cited by examiner

*Primary Examiner*—Howard J. Locker
*Assistant Examiner*—Kent L. Bell
(74) *Attorney, Agent, or Firm*—Christie, Parker & Hale, LLP

(57) ABSTRACT

A new plant of *Loropetalum chinense* characterized by its low growing, compact habit.

4 Drawing Sheets

BACKGROUND OF THE INVENTION

The present invention relates to a new and distinct variety of *Loropetalum chinense* and was discovered as a naturally occurring, whole-plant mutation in a cultivated planting of *Loropetalum chinense* in Angyo Kichi Zo, Saitama Prefecture, Japan. The varietal denomination of the new variety is 'Hindwarf'.

The genus Loropetalum is included in the family Hamamelidaceae that comprises about 15 genera of shrubs and trees growing in the northern hemisphere. Loropetalum comprises one species of evergreen shrub or small tree, which possesses desirable ornamental characteristics. Loropetalum was first introduced to Europe as an ornamental plant in the 1880s, and is believed to have been cultivated in North America since the early 1930s.

*Loropetalum chinense* is a native of China, and was first discovered in 1928 in Hunan province. It was rediscovered in the late 1980s and subsequently introduced to the United States. *Loropetalum chinense* generally has alternate, ovate leaves to 6 cm. long and 3 cm. wide. The plant is evergreen or partly evergreen depending on winter temperature. Leaf color ranges from light to dark burgundy, occasionally green, depending on light intensity, cultural conditions and cultivar. Shoots are slender, brown, and densely pubescent, pit is solid. Leaves are generally densely pubescent overall.

Flowers of *Loropetalum chinense* are perfect, four strap like, about 2 cm. long, and about 0.3 cm. wide petals. Three to six flowers are together in each leaf axil. Pedicel and calyx have a white pubescence. Flower color is pinkish to reddish purple depending on the cultivar. Flowering is heaviest in early spring.

SUMMARY OF THE INVENTION

The new variety was discovered as a naturally occurring, whole plant mutation in a cultivated planting of *Loropetalum chinense* and differs from other cultivars known to the inventor in having a low growing, compact habit. Asexual reproduction of the new variety by stem cuttings performed in Kawaguchi City, Saitama Prefecture, Japan; Lewisberry, Pa.; Irvine, Calif.; Forest Grove, Oreg. and Fulshear, Tex.; have confirmed that the distinctive characteristics of the new variety are stable and transmitted to succeeding generations and that the new variety reproduces true to type.

COMPARISON WITH PARENT

'Hindwarf' is distinguished from its parent and all other varieties of *Loropetalum chinense* of which I am aware by its prostrate, compact habit, reaching no more than 2 ft. in height and 3 to 6 ft. in width. In contrast, the parent of 'Hindwarf' is an upright-growing shrub to about 12 ft. high and 6 ft. wide. Named varieties similar to the parent include *Loropetalum chinense* 'Ruby' (unpatented), which reaches about 4 ft. high and about 3 ft. wide at maturity; and the variety 'Hines Purpleleaf' (unpatented), which reaches about 3 ft. high and about 2 ft. wide at maturity.

BRIEF DESCRIPTION OF ILLUSTRATIONS

The accompanying photographic illustrations show a plant of the new cultivar as true to color as is reasonably possible to make in an illustration of this character.

DETAILED DESCRIPTION OF THE NEW VARIETY

Figure 1:
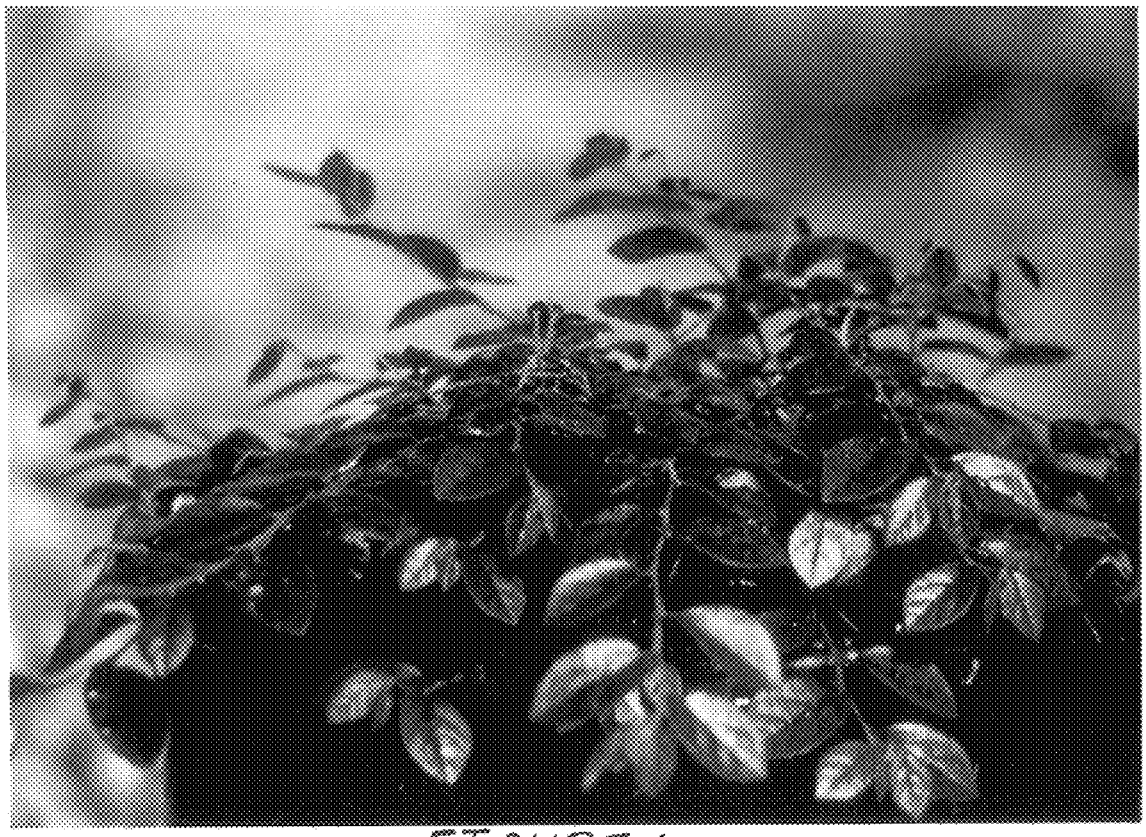
FIG. 1 illustrates the distinctive compact growth habit of a mature plant as well as the smaller leaf of a specimen grown in the United States.
Figure 2:
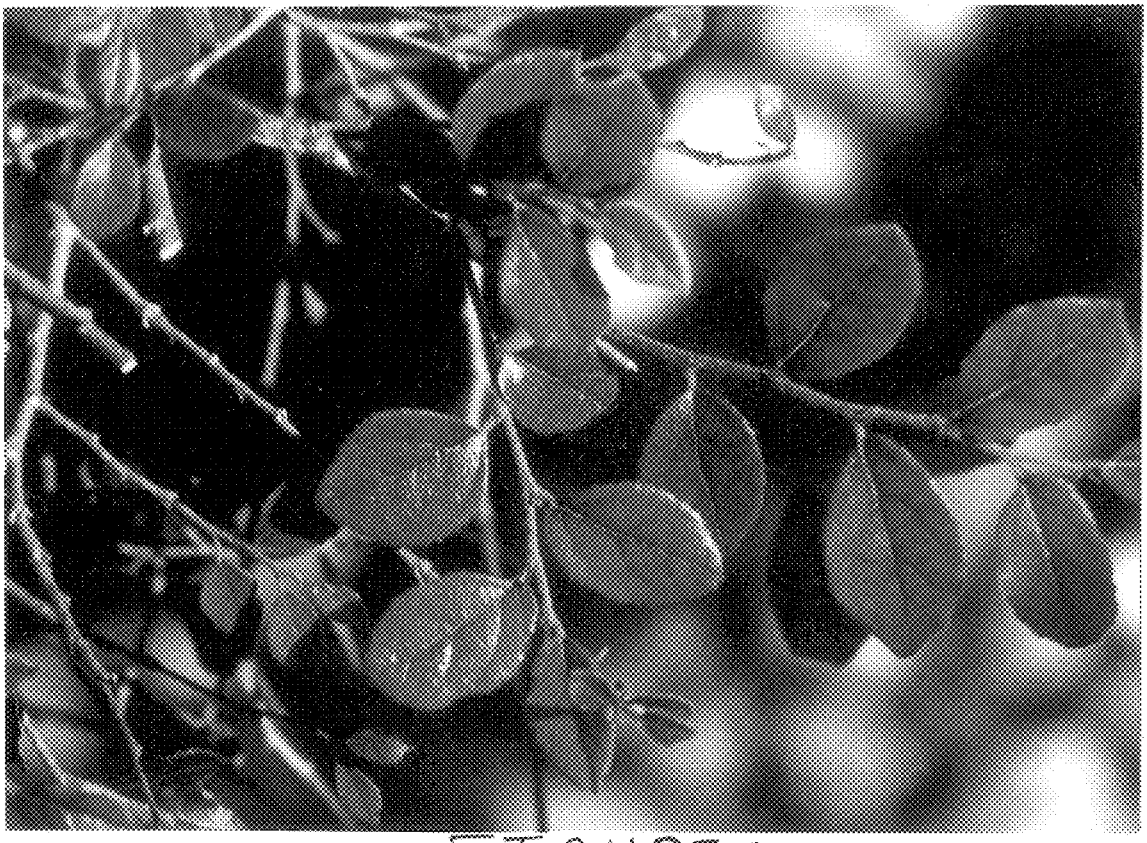
FIG. 2 illustrates the foliage of the new variety.
Figure 3:
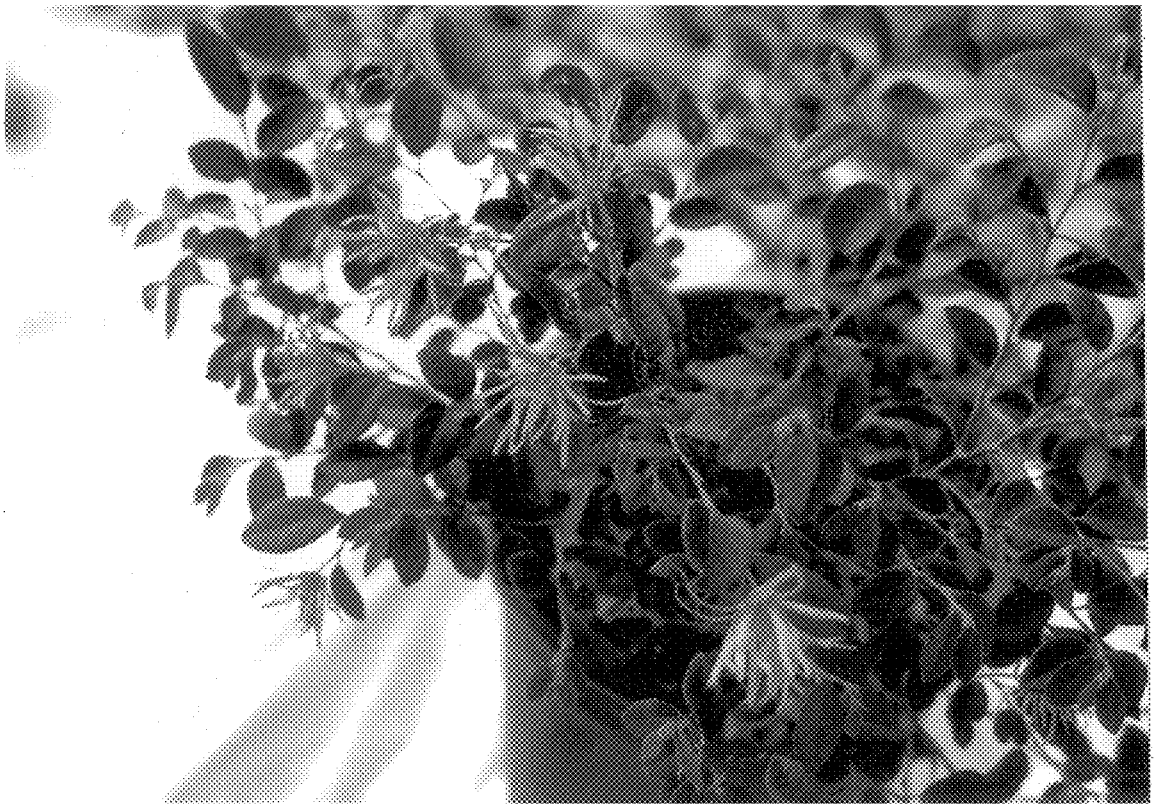
FIG. 3 illustrates the unique flower color and flower size.
Figure 4:
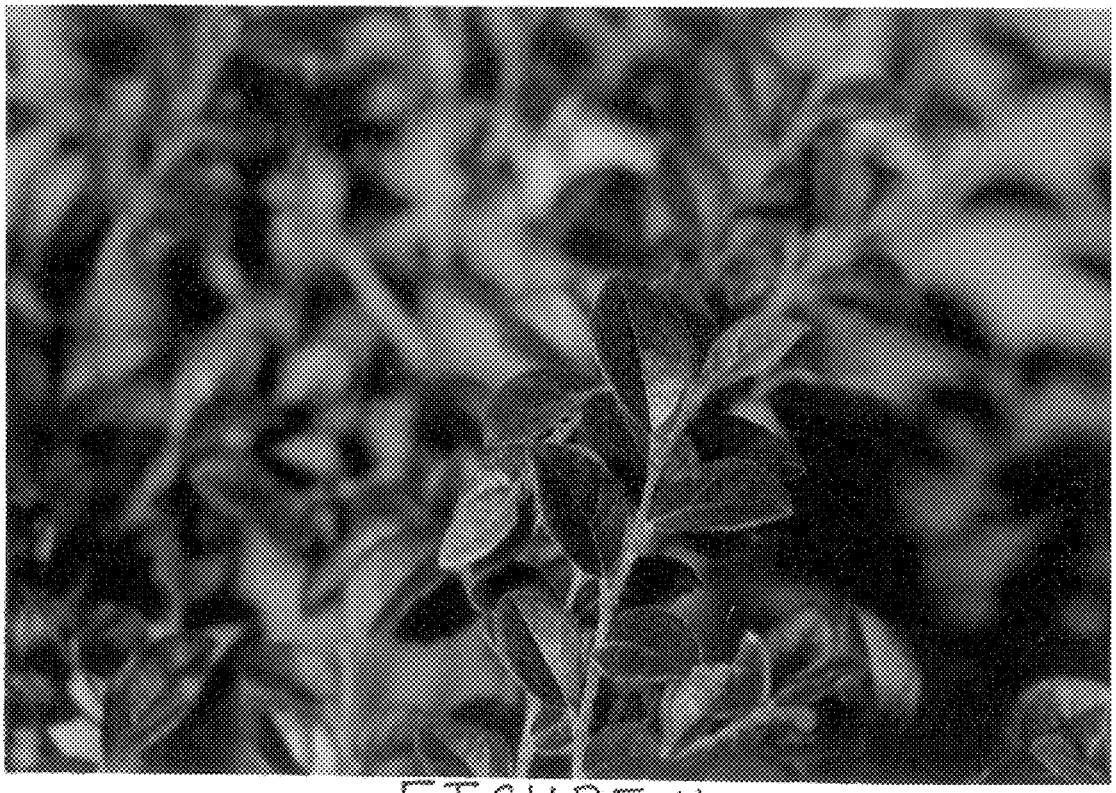
FIG. 4 illustrates the mature foliage of the new variety.

*Loropetalum chinense* 'Hindwarf' has not been observed under all possible environmental, cultural, and light conditions. The following observations and descriptions are of plants grown in containers at Fulshear, Tex. and Lewisberry, Pa., and of plants growing in the landscape in Katy, Tex. Phenotypic expression may vary with light intensity, cultural, and environmental conditions. In this description, color references are to The Royal Horticultural Society Colour Chart (1966) and terminology used in this color chart. As with many plants in the Hamamelidaceae family, phenotypic characteristics can be dramatically different in terms of growth morphology. For example, viewing this plant in Irvine, Calif., the growth habit is distinctly pendulous, growing down the pot and tending to have a horizontal growth form; in Fulshear, Tex. the plant is compact and upright with a mature height of about 2 feet.

Classification:
*Botanical.*—*Loropetalum chinense* 'Hindwarf'.
*Parentage.*—Whole plant mutation of an unnamed plant of *Loropetalum chinense.*
*Propagation.*—By vegetative cuttings.
Plant:
*Size.*—To approximately 2' tall and between about 3' to 6' wide.
*Branching.*—Dense, overall prostrate to mounding branching habit.
*Lateral branches.*—Multi-branched shrub.
*Branch number.*—More than 1,000 branches and stems.
*Branch size.*—Typical branch about 1 m. long, pendulous.
*Branch diameter.*—Typical branch about 1 cm. in diameter; branch apex is typically about 1 mm. or less.
*Branch coloration.*—Near Grayed-Orange Group 166B.
*Habit.*—Compact prostrate to mounding shrub.
*Leaf shape.*—Simple, alternate, ovate; obtuse to acute base, acute to obtuse apices.
*Leaf apex.*—Acute to obtuse.
*Leaf base.*—Obtuse to acute. Occasionally unequal.
*Leaf margin.*—Entire, with stellate hairs.
*Leaf texture/substance.*—Firm to leathery; upper surface and glossy, with impressed veins; underside glaucous with greenish veins and whitish midrib, with scattered stellate hairs.
*Leaf color.*—Varies with intensity of sunlight and cultural conditions; the following color readings were taken in April, November and December, of plants grown in full sun conditions.

April — Fulshear, Tex.

Young leaves:
*Upper side.*—Near Greyed-Purple Group 183A.
*Under side.*—Near Red-Purple Group 59C.
Mature leaves:
*Upper side.*—Near Yellow-Green Group 147A.
*Under side.*—Near Greyed-Green Group 191B.

November — Fulshear, Tex.

Young leaves:
*Upper side.*—Near Red Group 53A.
*Under side.*—Near Red Group 53D.
Mature leaves:
*Upper side.*—Near Greyed-Purple Group 187A.
*Under side.*—Near Red-Purple Group 59C with mottling near Yellow-Green Group 147B.

December — Fulshear, Tex.

Young leaves:
*Upper side.*—Near Greyed-Purple Group 187A.
*Under side.*—Near Red-Purple Group59C.
Mature leaves:
*Upper side.*—Near Green Group 133A.
*Under side.*—Near Yellow-Green Group 147A.

November — Vacaville, Calif.

Growth at base of branches:
*Upper side.*—Near Yellow-Green Group 147A.
*Under side.*—Near Yellow-Green Group 147B.
Growth at apex of branches:
*Upper side.*—Near Greyed-Purple Group 183A.
*Under side.*—Near Greyed-Purple Group 184D.
Venation:
*Pattern.*—Upper Surface: Pinnate. Under Surface: Pinnate.
Coloration:
*New foliage.*—Upper Surface: Near Near Greyed-Purple Group 187A. Under Surface: Near Red-Purple Group 59C.
*Mature foliage.*—Upper Surface: Near Green Group 133A. Under Surface: Near Yellow-Green Group 147A.
Petioles:
*Size.*—Approximately 1 to 3 mm. long; and approximately 0.8 mm. in diameter.
*Coloration.*—Near Greyed-Orange Group 166B (upper and lower surfaces).
Internodes: About 0.5 to 1.5 cm. long.
Leaf size: About 1 to 2.5 cm. long; 1 to 1.5 cm. wide.
Hardiness: USDA Zone 7 (0° F. to 7° F.).
Vigor: Moderate.
*March.*—Vacaville, Calif. About 7" high and about 12" wide.
*October.*—Vacaville, Calif. About 11" high, 30" wide.
Pests/diseases: No pest or disease problems noted.

Inflorescence

Bloom period: Early spring with occasional light repeat blooming throughout the growing season.
Flower form: Perfect, about 8 to 11 pinkish colored strap-like petals per flower.
Flower arrangement: Congested terminal raceme on short peduncle, occasionally solitary at terminals or in leaf axils; about 6 to 8 flowers per inflorescence.
Flower size: Approximately 1.5 to 2.0 cm long and about 1 to 2 mm wide.
Diameter: About 8 mm.
Depth: About 8 mm.
Lastingness of individual blooms: Between 2 and 3 weeks.
Fragrance: None noted.
Petals:
*Coloration.*—Upper Surface: From near Red Group 55B to 51A, 53C, 52A and 53D. Lower Surface: From near Red group 55B and 51A, 52A and 53D.
*Length/width.*—About 1.5 cm. long and about 1 mm. wide.
*Apex.*—Flat.
*Margin.*—Smooth.
Buds:
*Shape.*—2-horned capsule.
*Length.*—About 3 mm.
*Diameter.*—About 2 mm.
*Coloration.*—Near Red-Purple Group 60B.
Peduncle:
*Length.*—About 1 mm.
*Diameter.*—About 0.5 mm.
*Coloration.*—Light brown.

Reproductive organs

Stamens: 4.
Stigma: 1.
Pistils:
*Number.*—1.
Pollen:
*Amount produced.*—Minute.
*Color.*—Off-white.
Fruit:
*Type.*—Ovoid, woody, 2-horned capsule, one seed per each cell.
*Amount.*—About 75 to 100 per plant per year.
*Length.*—About 5 mm.
*Diameter.*—About 6 mm.
*Coloration.*—Dark brown.

I claim:

1. a new variety of Loropetalum plant, substantially as shown and described.

* * * * *